(12) United States Patent
Pierorazio

(10) Patent No.: US 6,991,365 B1
(45) Date of Patent: Jan. 31, 2006

(54) FLAMMABILITY TEST APPARATUS

(75) Inventor: Adrian Pierorazio, San Antonio, TX (US)

(73) Assignee: Baker Engineering and Risk Consultants, Inc., San Antonio, TX (US)

(*) Notice: Subject to any disclaimer, the term of this patent is extended or adjusted under 35 U.S.C. 154(b) by 53 days.

(21) Appl. No.: 10/146,901

(22) Filed: May 17, 2002

(51) Int. Cl.
*G01N 25/00* (2006.01)

(52) U.S. Cl. ............................................. 374/8; 374/38
(58) Field of Classification Search ................... 374/8, 374/36, 37, 38; 73/36, 35.17, 35.14, 35.15, 73/35.16, 865.6; 137/543.15
See application file for complete search history.

(56) References Cited

U.S. PATENT DOCUMENTS

| | | | | |
|---|---|---|---|---|
| 2,500,964 A | * | 3/1950 | Sullivan et al. ............... | 73/36 |
| 2,659,235 A | * | 11/1953 | Storer ........................ | 73/865.6 |
| 2,679,860 A | * | 6/1954 | Diebold ...................... | 73/865.6 |
| 2,917,927 A | * | 12/1959 | Clark ......................... | 73/865.6 |
| 2,937,530 A | * | 5/1960 | Haley ......................... | 73/865.6 |
| 3,545,252 A | * | 12/1970 | Springfield et al. ............ | 374/8 |
| 3,590,559 A | * | 7/1971 | Bragg et al. ................. | 714/764 |
| 3,593,563 A | * | 7/1971 | Marmor et al. ................ | 374/8 |
| 3,605,483 A | * | 9/1971 | Ringwald et al. .............. | 374/8 |
| 3,662,586 A | * | 5/1972 | Suga .......................... | 374/8 |
| 3,667,277 A | * | 6/1972 | Miller et al. ................. | 374/8 |
| 3,987,661 A | * | 10/1976 | Kamp et al. .................. | 374/8 |
| 4,059,007 A | * | 11/1977 | Miller et al. ................. | 374/8 |
| 4,140,004 A | * | 2/1979 | Smith et al. .................. | 374/8 |
| 4,485,739 A | * | 12/1984 | Emmett ....................... | 102/200 |
| 4,682,495 A | * | 7/1987 | McNeely ...................... | 73/168 |
| 4,695,703 A | * | 9/1987 | Williams et al. .............. | 219/212 |
| 4,973,451 A | * | 11/1990 | Vickery ....................... | 422/110 |

(Continued)

FOREIGN PATENT DOCUMENTS

| | | | |
|---|---|---|---|
| JP | 2001337060 A | * | 12/2001 |
| JP | 2003146399 | * | 5/2003 |

OTHER PUBLICATIONS

Ale, et al., "The Flammability Limits Of Hydrogen And Methane In Air At Moderately Elevated Temperatures", Energy Conversion Engineering Conference, IECEC-97, Proceedings of the 32nd Intersociety, Jul. 27-Aug. 1, 1997, vol. 2, page(s): 938-943.*

(Continued)

*Primary Examiner*—Gail Verbitsky
*Assistant Examiner*—Mirellys Jagan
(74) *Attorney, Agent, or Firm*—McDermott Will & Emery LLP

(57) ABSTRACT

A flammability test apparatus comprises a chamber, an inlet, an ignition source, a heater, and pressure and temperature sensors. In one embodiment, the chamber includes a horizontally-oriented, cylindrically-shaped section. The inlet allows a fluid to be introduced into the chamber. The ignition source ignites the fluid within the chamber, and the heater adjusts the temperature of the fluid within the chamber. The test apparatus includes a sparger for dispersing the fluid within the chamber, and the sparger disposed within the chamber and attached to the inlet. The test apparatus also includes a relief system for exhausting the chamber after the pressure of the fluid in the chamber exceeds a preset pressure.

37 Claims, 4 Drawing Sheets

U.S. PATENT DOCUMENTS

| | | | | |
|---|---|---|---|---|
| 4,990,312 A | * | 2/1991 | Rucker et al. | 374/8 |
| 5,364,262 A | * | 11/1994 | Phillips | 431/202 |
| 5,779,466 A | * | 7/1998 | Okamura | 431/89 |
| 5,918,679 A | * | 7/1999 | Cramer | 169/45 |
| 5,932,796 A | * | 8/1999 | Arthaud et al. | 374/8 |
| 6,342,186 B1 | * | 1/2002 | Wingfield et al. | 422/102 |
| 6,471,507 B1 | * | 10/2002 | Hall | 374/8 |
| 2002/0092568 A1 | * | 7/2002 | Sims | 137/543.15 |

OTHER PUBLICATIONS

Inculet, et al., "Ignition Studies Of Selected Explosive Mixtures Of Gases And Dusts Emitted From Cement Kilns", Industry Applications Society Annual Meeting, Conference Record of the 1990 IEEE, Oct. 7-12, 1990, vol. 1, page(s): 888-892.*

* cited by examiner

FLAMMABILITY TEST APPARATUS

FIELD OF THE INVENTION

The invention relates generally to testing equipment and, more specifically, to a test apparatus for testing the flammability of certain mixtures of gases.

BACKGROUND OF THE INVENTION

There is often a need to determine the conditions at which certain mixtures of fluids, more specifically, gases, become flammable for the purposes of process design and/or safety development. Depending upon the application, it may be desirable to have a mixture of gases be flammable, or alternatively, it may be desirable to have a mixture of gases not be flammable. Thus, depending upon certain baseline conditions, such as temperature, pressure, or percent concentration, it is desirable to discover how certain combinations of conditions affects whether the mixture of gases is flammable or not. FIGS. 1A, 1B are illustrative examples of how the flammability of a gas mixture, for example, a fuel gas, oxygen, and an inert gas, changes depending upon the baseline conditions involved. In FIG. 1A, the baseline conditions are a pressure of 100 psig and a temperature of 100° C. In FIG. 1B, the baseline conditions are a pressure of 400 psig and a temperature of 100° C.

The data points in FIGS. 1A and 1B are obtained using a test apparatus that determines whether the gas mixture is flammable. The test apparatus is typically a spherical chamber into which the gas mixture is introduced. The spherical shape of the chamber maximizes the gas pressure that can be introduced into the chamber. A spherical chamber also allows for easier mixing of the gas within the chamber because a sphere does not contain any "dead zones" in which the gas can be trapped. However, a spherical chamber is expensive to manufacture, and the relative height to width of the spherical chamber may produce stratification within the chamber such that the composition of the gas mixture varies in a vertical direction. The expense of the spherical chamber is magnified because the spherical chamber must have a design burst pressure that exceeds the pressure in the chamber after the gases have been ignited. As a rule of thumb, the pressure in the chamber after the gases have been ignited is approximately eight times the pressure of the gases before ignition.

There is, therefore, a need for an improved test apparatus that is less expensive to manufacture but still provides good gas distribution throughout the chamber. Furthermore, there is a need to eliminate the necessity to form a chamber whose burst pressure is at least eight times greater than the highest initial pressure of gases being tested within the chamber. Still further, there is a need for a test apparatus that reduces stratification of gases within the test chamber.

SUMMARY OF THE INVENTION

These and other needs are met by a test apparatus of the present invention, which in accord with one aspect includes a chamber, an inlet, an ignition source, a heater, and pressure and temperature sensors. The inlet introduces fluid into the chamber, and the ignition source ignites the fluid within the chamber. The heater adjusts the temperature of the fluid within the chamber. In one embodiment, the chamber is a horizontally-oriented, cylindrically-shaped section. The test apparatus includes a sparger for dispersing the fluid within the chamber, with the sparger disposed within the chamber and attached to the inlet. The test apparatus also includes a relief system for exhausting the chamber after the pressure of the fluid in the chamber exceeds a preset pressure.

Providing a cylindrically-shaped section allows for ease of manufacture. In combination with the sparger, this arrangement improves the distribution of the fluid within the chamber. The relief system allows the chamber to be built to withstand less pressure and/or allow for higher pressures of fluid to be tested within the chamber.

In another aspect of the test apparatus, the heater is positioned around the outside of the cylindrically-shaped section. The test apparatus also includes an outlet for exhausting the chamber.

In still another aspect of the test apparatus, the sparger is oriented substantially parallel to the longitudinal axis of the cylindrically-shaped section. Also, the sparger is oriented towards the upper portion of the cylindrically-shaped section, and the sparger extends at least 75% of the longitudinal axis of the cylindrically-shaped section. The sparger includes outlets which can be positioned either in-line or in groups along a cross-section of the sparger with each group including radially-oriented outlets. The sparger provides a substantially even distribution of the fluid throughout the chamber.

In yet another aspect of the test apparatus, the relief system activates when the pressure of the fluid in the chamber exceeds a preset pressure. The relief system includes a cover covering an opening in the chamber, and the cover is movably attached to the chamber. The relief system also includes at least one spring that exerts force against the cover to seal the cover against the chamber. The force exerted by the at least one spring determines the preset pressure. The set pressure of the relief system is adjustable, and is less than the burst pressure of the chamber.

Additional advantages of the present invention will become readily apparent to those skilled in this art from the following detailed description, wherein only an exemplary embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DETAILED DESCRIPTION

Figure 2:
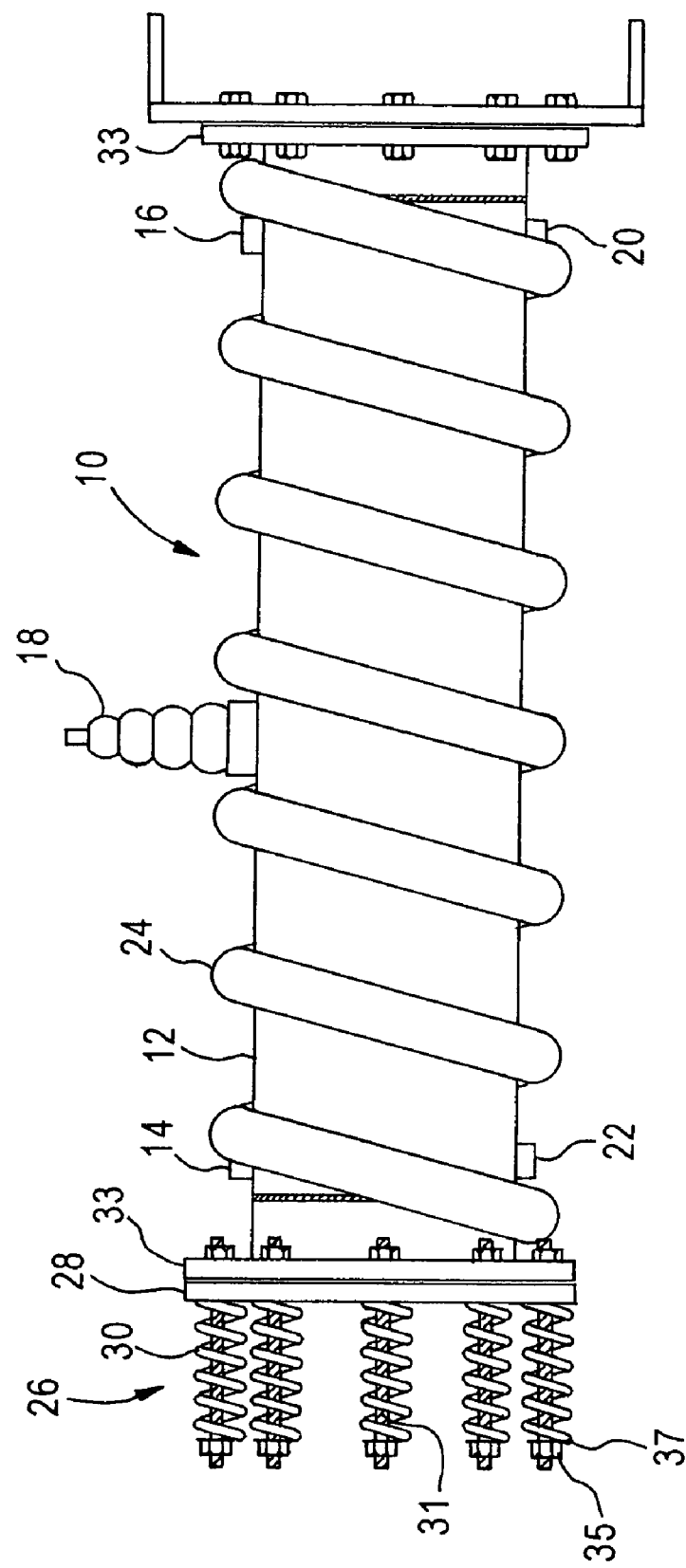
FIG. 2 is a schematic side view of a testing apparatus in accord with one aspect of the invention.

A test apparatus, in accordance with an aspect of the invention, is illustrated in FIG. 2. The test apparatus 10 includes a chamber 12, gas supply line 14, vent 16, and an ignition source 18. The gas supply line 14 supplies a fluid, such as a gas mixture to be tested, into the chamber 12. The ignition source 18 is also connected to the chamber 12 and is used as a catalyst to determine whether the gas in the chamber 12 ignites. The test apparatus 10 is not limited in the manner in which the gas is released from the chamber 14. For example, the gas can be released from the chamber 12 via the gas supply line 14. However, in one aspect of the test apparatus, a separate vent or exhaust line 16 is attached to the chamber 12.

The test apparatus 10 can also include a pressure sensor 20 and a temperature sensor 22 for respectively sensing the pressure and temperature within the chamber 12. A heater 24 can be wrapped around the chamber 12 to adjust the temperature within the chamber 12. A relief system 26 can also be attached to the chamber 12 to provide pressure relief to the chamber 12 when the pressure in the chamber 12 exceeds a set pressure.

The chamber 12 is not limited as to a particular shape. For example, the chamber 12 can be spherical. However, in at least one aspect of the test apparatus 10, the chamber 12 includes a cylindrically-shaped section. Although not capable of withstanding as much pressure as a similarly configured spherical chamber, a cylindrical chamber 12 is easier to manufacture than a spherical chamber.

Figure 5:
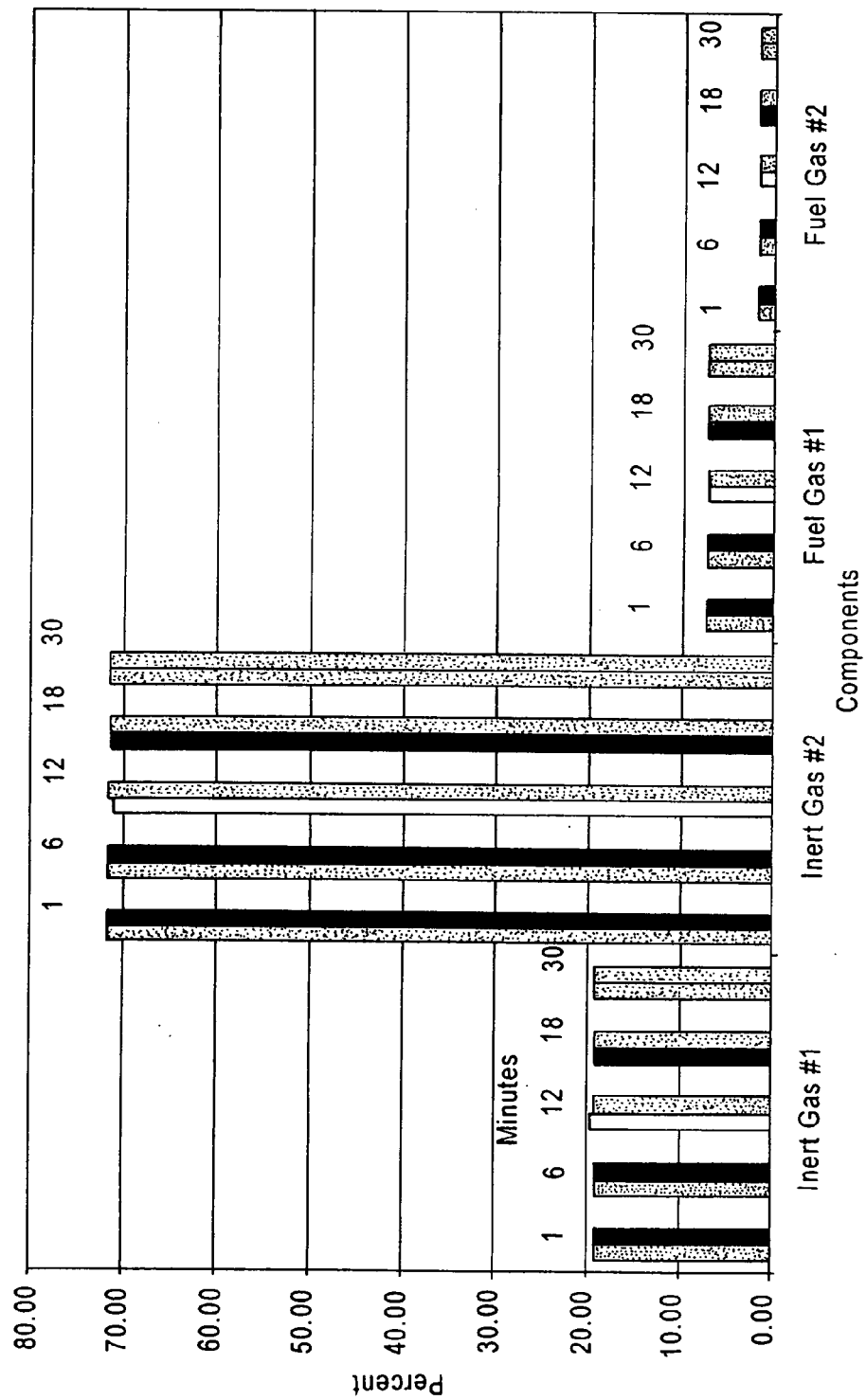
FIG. 5 is a table showing the distribution of gas mixture constituents in a chamber over time.

The cylindrical chamber 12 is not limited as to a particular orientation when in use. However, in at least one aspect of the test apparatus 10, the longitudinal axis L of the cylindrical chamber 12 is oriented substantially horizontal (also shown in FIG. 3). When the aspect ratio (length/diameter) of the chamber 12 is greater than one, by orienting the longitudinal axis substantially horizontally, stratification of gases within the chamber 12 is reduced. For example, FIG. 5 illustrates how little the composition of gases vary from the top of the chamber 12 to the bottom of the chamber 12. As such, the horizontally oriented cylindrical chamber 12 provides reduced stratification of gases within the chamber 12.

The aspect ratio of the chamber 12 is not limited as to a particular range. However, as the aspect ratio increases for a given volume of the chamber 12, the ends of the chamber 12 are increasingly distant from the ignition source 18. As such, the gases located at the ends of the chamber 12 are less exposed to the ignition source 18, and if the gases are located sufficiently far enough away from the ignition source 18, the gases will not be affected by the strength of the ignition source 18. Therefore, in at least one aspect of the testing apparatus 10, the aspect ratio of the cylindrically-shaped chamber 12 is less than six.

Figures 1A, 1B:
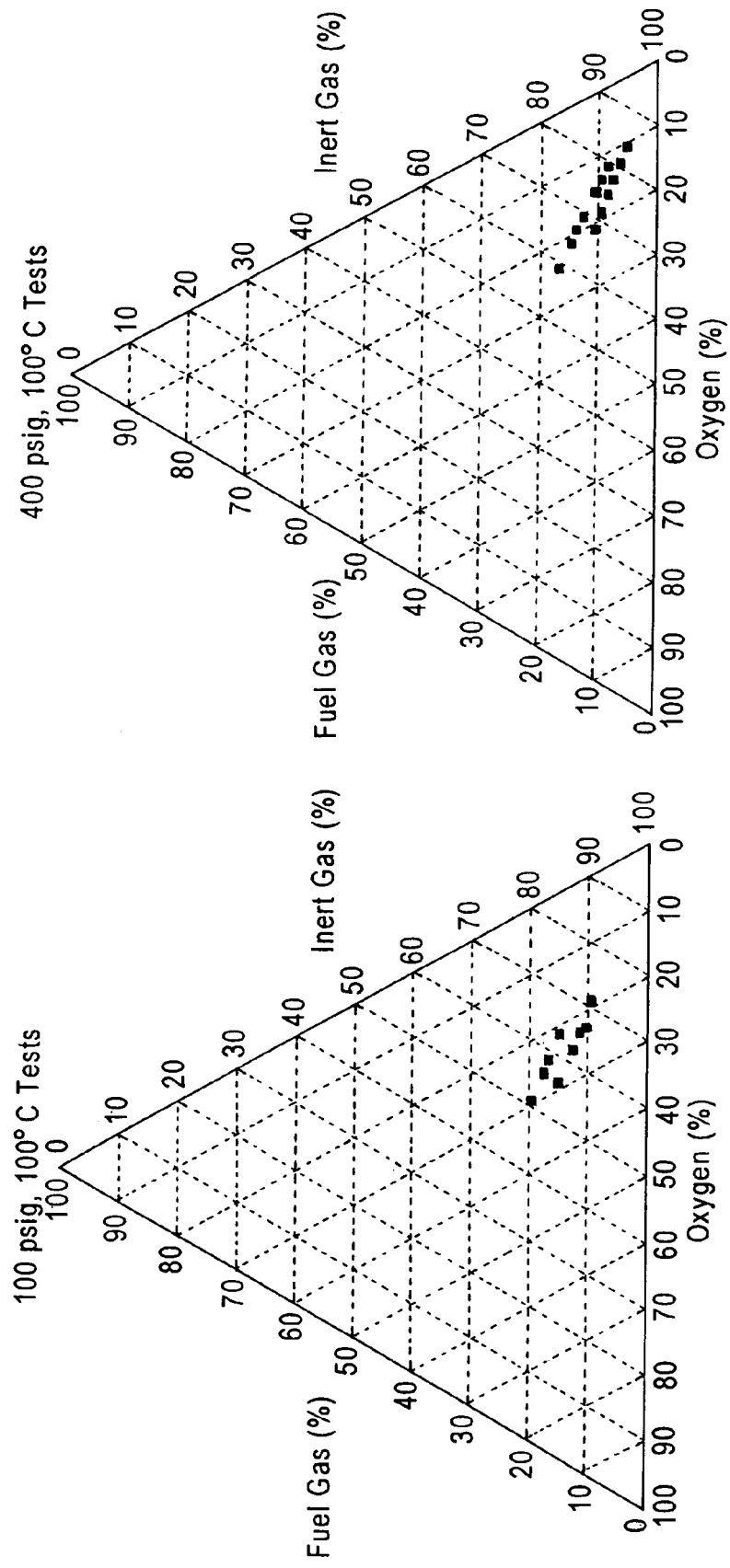
FIGS. 1A and 1B are triangular plots of flammability test results.

Referring back to FIG. 1, the testing apparatus 10 is not limited as to a particular type of ignition source 18. However, in certain aspects of the test apparatus 10, the ignition source 18 replicates a potential source of ignition that that gases being test might encounter in a real-world situation. For example, the potential source of ignition can be a flame, and the ignition source 18 can therefore be selected so as to replicate a flame. In at least one aspect of the testing apparatus 10, however, the ignition source 18 provides a electric spark, which can replicate, for example, an electrical short or a static discharge. One example of an ignition source 18 that replicates an electric spark is a spark plug.

The testing apparatus 10 is not limited as to the placement of the ignition source 18 within the chamber 12 or the number of ignition sources 18 within the chamber 12. However, in at least one aspect of the testing apparatus 10, one ignition source 18 is substantially (vertically and horizontally) centrally located within the chamber 12. By centrally locating the ignition source 18 within the chamber 12, the cumulative average distance between the ignition source 18 and the gas within the chamber 12 is reduced, which increases the exposure of the gas to the ignition source 18.

One potentially important parameter during flammability testing of gas mixtures is the temperature of the gas during testing. As such, the testing apparatus 10 can include a temperature sensor 22 for measuring temperature of the gas directly or by inferentially measuring the temperature of the gas by measuring the temperature of the chamber 12. Many different types of temperature sensors 22 are known in the art, and the testing apparatus 10 is not limited as to a particular type of temperature sensor 22. For example, if the temperature of the gas is being measured inferentially, the temperature sensor 22 can be a thermocouple attached to the outside circumference of the chamber 12.

The testing apparatus 10 can also include a heater 24 for adjusting the temperature of the gas within the chamber 12. Many different types of heaters 24 are known in the art, and the testing apparatus 10 is not limited as to a particular type of heater 24. For example, the heater 24 can be a heating blanket wrapped around the outside of the chamber 12. However, in at least one aspect of the testing apparatus, the heater 24 is a flexible coil-shaped heater that is wrapped around the outside of the chamber 12.

The testing apparatus 10 can include one or more relief systems 26 located on the chamber 12. The pressure within the temperature apparatus 10 can increase up to eight fold or higher during a flammability test upon the ignition of the gases within the chamber 12. As such, prior art chambers are typically designed to withstand at least eight times the pressure of the initial pressure of the gases being introduced into the chamber. However, by including a relief system 26 within the testing apparatus 10, the relief system 26 can act to relieve pressure within the chamber 12 if the pressure exceeds a certain set amount. Therefore, the use of a relief system 26 allows the chamber 12 to be built to withstand a significantly lower pressure compared to a chamber 12 without a relief system 26. Thus, the chamber 12 can be built to withstand less pressure (thereby being less expensive to manufacture) and/or allow higher pressures of gases to be tested within the chamber 12.

Any relief system 26 capable of relieving pressure from a chamber 12 after the pressure in the chamber 12 reaches a predetermined set amount is acceptable for use with the testing apparatus 10. However, in at least one aspect of the testing apparatus 10, the relief system 26 includes a cover 28 and multiple springs 30 exerting a force against the cover 28. The springs 30 can be supported on and guided by rods 31 that pass through the cover 28 and are attached to the chamber 12. A nut 35 threaded onto the rod 31 inside the spring 30 can serve as an adjustable cover travel stop. A threaded nut 35 and washer 37 pre-load assembly placed onto the rod 31 above the spring 30 allows the amount of force exerted by the spring 30 to be varied.

Although not limited in this manner, the relief system 26 can be attached to at least one of the heads 33 of chamber 12. The heads 33 of the chamber 12 are located at the end of the cylindrical section of the chamber 12 and are not limited as to a particular shape. For example, the heads 33 can be semi-spherical. In a current aspect of the test apparatus 10, however, the heads 33 are substantially flat, round plates, which allows for ease of manufacture. Furthermore, the relief system 26 can be incorporated into the head 33 by using the substantially flat plate of the head 33 as the cover 28 of the relief system 26.

Figure 3:
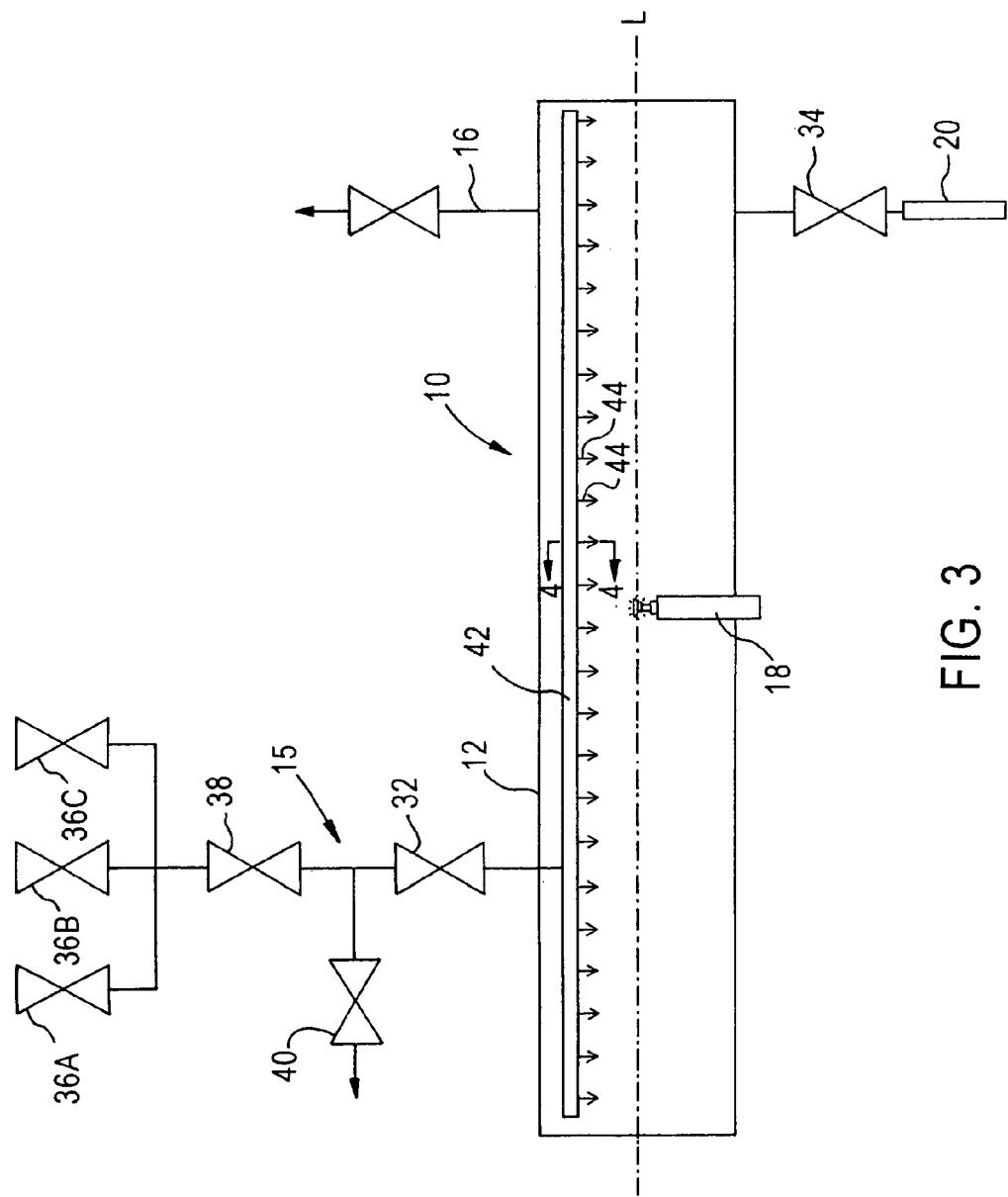
FIG. 3 is a cross-sectional side view of a testing apparatus.

As illustrated in FIG. 3, the inlet 14 may include a gas supply line 15 attached to the chamber 12 to introduce the gas into the chamber 12. Although not necessary, the gas supply line 15 can include a block 32 that prevents any combustion products from going up the gas supply line 15, and any block 32 so capable is acceptable for use with the testing apparatus 10. For example, the block 32 can be a check valve that allows the gas to enter the chamber 12 but doesn't allow gas out of the chamber 12 via the gas supply line 15.

The gas supply line 15 is connected to the source 36 of the gas. For example, if the mixture of gas includes oxygen, a fule gas, and an inert gas, the gas supply line 15 can be connected to three separate sources 36A–C for each constituent of the gas mixture. Alternatively, the gas supply line 15 can be connected to a single source 36 that contains the final mixture of the gases.

The gas supply line 15 can also include a main valve 38 that regulates the flow of the gas mixture into the chamber 12. If a block 32 is being used, the gas supply line 15 can also include a bleed valve 40 that allows gas between the block 32 and the main valve 38 to be bled off after the main valve 38 has been closed.

A manifold or sparger 42 (hereinafter referred to as sparger) can be disposed within the chamber 12 and attached to the inlet 14. The sparger 42 receives the gas from the gas supply line 15 via the inlet 14 and distributes the gas within the chamber 12. Many types of spargers 42 are known capable of distributing gas into a chamber 12, and the testing apparatus 10 is not limited as to a particular type of sparger 42.

In at least one aspect of the testing apparatus 10, the sparger 42 is longitudinally disposed substantially parallel to the longitudinal axis L of the chamber 12. In this manner, the sparger 42 can supply the gas to greater portions of the chamber 12. Furthermore, in certain aspects of the testing apparatus 10, the sparger 42 extends at least 75% of the length of the longitudinal axis of the chamber 12. In other aspects, the sparger 42 extends at least 90% of the length of the longitudinal axis of the chamber 12. In so doing, the sparger 42 can better supply the gas to ends of the chamber 12.

Although not limited in this manner, the sparger 42 can evenly distribute the gas within the chamber 12. When the longitudinal axis L of the chamber 12 is located horizontally, the sparger 42 can be located in a top portion of the chamber 12. In certain aspects, the sparger 42 is located in a top 35% of the chamber 12, and in other aspects, the sparger 42 is located in a top 20% of the chamber 12. In so doing, an even distribution of gas within the chamber 12 can be provided because placing the sparger 42 near the top of the chamber 12 reduces stratification of gases within the chamber 12 from heavier gases accumulating near the bottom of the chamber 12.

Figure 4A:
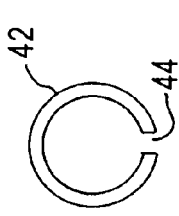
FIG. 4A is a cross-sectional view taken along line 4—4 in FIG. 3.
Figure 4B:
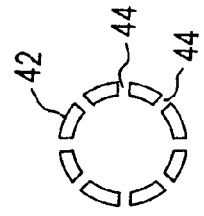
FIG. 4B is an alternate embodiment of the sparger shown in FIG. 4A.

The sparger 42 includes outlets 44 through which the gas passes into the chamber 12. Although not limited in this manner, as illustrated in FIG. 4, the outlets 44 can be positioned in-line along the length of the sparger 42 (as shown in FIG. 4A). Alternatively, the outlets 44 can be distributed about the cross-section and radially oriented (as shown in FIG. 4B). In either manner, an even distribution of gas within the chamber 12 can be provided.

One potentially important parameter during flammability testing of gas mixtures is the pressure of the gas mixture during testing. Also, one measure as to whether the gases in the chamber 12 have ignited is whether or not the pressure in the chamber 12 increases. As such, referring back to FIG. 3, the testing apparatus 10 can include a pressure sensor 20 connected to the chamber 12 for measuring the pressure within the chamber 12. Many different types of pressure sensors 20 are known in the art, and the testing apparatus 10 is not limited as to a particular type of pressure sensor 20. However, in at least one aspect of the testing apparatus, the pressure sensor 20 is at least partially shock resistant so as to resist a shock created by the ignition of gases within the chamber 12.

Although not limited in this manner, the testing apparatus 10 can include a transmitter block 34 disposed between the pressure sensor 20 and the chamber 12. The transmitter block 34 acts to prevent the pressure sensor 20 from being exposed to adverse conditions. For example, if the gas in the chamber 12 ignites, the pressure sensor 20 can be exposed to both high heat and pressure, which could damage the pressure sensor 20. However, by using a transmitter block 34 to isolate the pressure sensor 20 from the chamber 12 at the time of flammability testing, the pressure sensor 20 need not be exposed to any potentially damaging conditions. After the test has been completed, the transmitter block 34 can be disengaged, and the pressure sensor 20 can sense the pressure within the chamber 12. Although any transmitter block 34 capable of the foregoing is acceptable for use with the testing apparatus 10, in at least one aspect of the testing apparatus 10, the transmitter block 34 is a valve that is electrically triggered to activate immediately before the ignition source 18 activates and to deactivate once the ignition source 18 has stopped firing.

Although any testing procedure can be used with the testing apparatus 10 of the present invention, an example testing procedure is provided as follows. Initially, the gas supply line 14, chamber 12, and vent 16 are purged of all residual gases. In particular, the chamber 12 can be purged twice using a non-reactive gas, such as nitrogen. The chamber 12 is then heated to a temperature slightly higher than the desired temperature of the gas mixture. When the gas mixture is introduced into the chamber 12, the heated chamber 12 increases the temperature of the gas mixture until the gas mixture reaches the desired temperature. The chamber 12 is then filled with the desired gas mixture.

FIG. 5 illustrates the uniformity of the gas mixture within the testing apparatus 10. Measurements were taken at the top and bottom of the chamber 12, at the center of the chamber 12 near the ignition source 18, and along the longitudinal axis adjacent to the ends of the chamber 12 show that there is no appreciable stratification in the chamber, as top and bottom pairs are nearly identical at each time interval, and there is no measurable longitudinal variation in the mixture.

Once the desired gas mixture is within the chamber 12, the main valve 38 is closed and the bleed valve 40 is opened to release any gas mixture remaining in the gas supply line 14. After a period of time in which the gas mixture is allowed to mix and stabilize within the chamber 12, the transmitter block 34 is activated and the ignition source 18 is fired. If it is determined that the gas mixture has not ignited, the ignition source 18 can be refired a number of times to ensure that the gas mixture does not ignite at the conditions being tested. Once the ignition source 18 has been fired, the pressure within the chamber 12 is checked. If a pressure increase is recorded, the chamber 12 is exhausted using the vent 16 and the whole procedure can be repeated.

If the pressure has not increased, the ignition source 18 can be refired, as discussed above.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only an exemplary aspect of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A test apparatus for conducting flammability testing on a fluid, comprising:
    a chamber comprising an outer wall and a cylindrically-shaped section having a longitudinal axis oriented horizontally, the cylindrically-shaped section including a portion of the outer wall;
    an inlet connected to the chamber;
    a sparger disposed within the chamber and attached to the inlet; and,
    an ignition source disposed within the chamber, wherein the sparger extends about 75% of the longitudinal axis of the cylindrically-shaped section or greater.

2. The test apparatus according to claim 1, wherein the chamber has an aspect ratio of greater than about 1.

3. The test apparatus according to claim 1, wherein the chamber has an aspect ratio of less than about 6.

4. The test apparatus according to claim 1, wherein the sparger is disposed in an upper portion of the chamber.

5. The test apparatus according to claim 1, wherein the sparger extends about 90% of the longitudinal axis of the cylindrically-shaped section or greater.

6. The test apparatus according to claim 1, wherein the inlet comprises a supply line, a main valve, check valve, and a bleed valve.

7. The test apparatus according to claim 1, wherein the sparger comprises a pipe having a plurality of outlets.

8. The test apparatus according to claim 7, wherein the outlets are arranged in-line.

9. The test apparatus according to claim 7, wherein the outlets are arranged radially.

10. The test apparatus according to claim 1, further comprising a heater attached to the chamber.

11. The test apparatus according to claim 10, wherein the heater comprises a flexible coil and is at least partially wrapped around the outer surface of the chamber.

12. The test apparatus according to claim 10, wherein the heater comprises a blanket and is at least partially wrapped around the outer surface of the chamber.

13. The test apparatus according to claim 1, further comprising a relief system attached to the chamber.

14. The test apparatus according to claim 13, wherein the relief system includes a preset pressure setting, and the relief system activates after a pressure in the chamber exceeds the preset pressure setting.

15. The test apparatus according to claim 14, wherein the preset pressure setting is adjustable.

16. The test apparatus according to claim 14, wherein the relief system comprises,
    a plate covering an opening in the chamber and movably attached to the chamber, and
    at least one spring exerting force against the plate to seal the plate against the chamber and the force exerted by the at least one spring determines the preset pressure.

17. The test apparatus of claim 16, wherein the chamber has a head disposed at an end of the cylindrically-shaped section of the chamber, and the relief system plate consists of the head.

18. A test apparatus for conducting flammability testing on a fluid, comprising:
    a chamber having a longitudinal axis;
    an inlet line connected to the chamber;
    an ignition source in the chamber for igniting the fluid;
    a heater attached to the chamber;
    a relief system connected to the chamber, the relief system activated in response to a pressure in the chamber exceeding a predetermined pressure and deactivated in response to the pressure in the chamber falling; and
    a sparger disposed within the chamber and attached to the inlet line;
    wherein the sparger comprises a pipe having a plurality of outlets and extends about 75% of the longitudinal axis of the chamber or greater.

19. The test apparatus according to claim 18, wherein the inlet line comprises a supply line, a main valve, check valve, and a bleed valve.

20. The test apparatus according to claim 18, wherein the ignition source is centrally disposed within the chamber in both vertical and horizontal directions.

21. The test apparatus according to claim 18, wherein the ignition source provides a flame.

22. The test apparatus according to claim 18, wherein the ignition source provides an electric spark.

23. The test apparatus according to claim 18, wherein the heater comprises a flexible coil and is at least partially wrapped around the outer surface of the chamber.

24. The test apparatus according to claim 18, wherein the heater comprises a blanket and is at least partially wrapped around the outer surface of the chamber.

25. The test apparatus according to claim 18, wherein the outlets are arranged in-line.

26. The test apparatus according to claim 18, wherein the outlets are arranged radially.

27. The test apparatus according to claim 18, wherein the sparger extends about 90% of the longitudinal axis of the chamber or greater.

28. The test apparatus according to claim 1, further comprising a temperature sensor for measuring pressure within the chamber.

29. The test apparatus according to claim 18, further comprising an outlet line connected to the chamber.

30. The test apparatus according to claim 18, wherein the predetermined pressure required to activate the relief system is adjustable.

31. The test apparatus according to claim 18, further comprising a pressure sensor for measuring pressure within the chamber.

32. The test apparatus according to claim 31, further comprising a transmitter block for protecting the pressure sensor.

33. The test apparatus according to claim 18, wherein the relief system comprises a cover movably attached to the chamber, a guide rod attached to the cover, a spring disposed around the guide rod, and a nut attached to the guide rod.

34. The test apparatus of claim 33, wherein the chamber has a head disposed at an end of a cylindrically-shaped section of the chamber, and the relief system cover consists of the head.

35. The test apparatus according to claim 18, wherein the chamber comprises a cylindrically-shaped section along the longitudinal axis, which is horizontally oriented.

36. The test apparatus according to claim 35, wherein the chamber has an aspect ratio greater than about 1.

37. The test apparatus according to claim 35, wherein the chamber has an aspect ratio of less than about 6.

* * * * *